United States Patent
Sasaki et al.

(10) Patent No.: US 9,433,399 B2
(45) Date of Patent: Sep. 6, 2016

(54) ULTRASOUND DIAGNOSIS APPARATUS, IMAGE PROCESSING APPARATUS, AND IMAGE PROCESSING METHOD

(71) Applicant: Toshiba Medical Systems Corporation, Otawara-shi (JP)

(72) Inventors: Takuya Sasaki, Nasu-gun (JP); Ryota Osumi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/078,696

(22) Filed: Nov. 13, 2013

(65) Prior Publication Data

US 2014/0064591 A1 Mar. 6, 2014

Related U.S. Application Data

(63) Continuation of application No. PCT/JP2012/066886, filed on Jul. 2, 2012.

(30) Foreign Application Priority Data

Jun. 30, 2011 (JP) ................................ 2011-146254

(51) Int. Cl.
*A61B 8/00* (2006.01)
*A61B 8/08* (2006.01)
(Continued)

(52) U.S. Cl.
CPC ............. *A61B 8/5223* (2013.01); *A61B 5/125* (2013.01); *A61B 8/00* (2013.01); *A61B 8/5207* (2013.01); *A61B 8/5269* (2013.01); *A61B 6/5205* (2013.01); *G01S 7/52077* (2013.01)

(58) Field of Classification Search
USPC .................................................. 382/128, 260
See application file for complete search history.

(56) References Cited

U.S. PATENT DOCUMENTS 5,799,112 A * 8/1998 de Queiroz et al. .......... 382/254
6,768,518 B1 * 7/2004 Bozdagi ........................ 348/615
(Continued)

FOREIGN PATENT DOCUMENTS

JP  2005-296331 A  10/2005
JP  2006-204594 A  8/2006
(Continued)

OTHER PUBLICATIONS

Zhang, Ming, Gunturk, Bahadir K. "Multiresolution Bilateral Filtering for Image Denoising" IEEE Transactions on Image Processing, vol. 17 No. 12, Dec. 2008.*

(Continued)

*Primary Examiner* — Kim Vu
*Assistant Examiner* — Molly Delaney
(74) *Attorney, Agent, or Firm* — Oblon, McClelland, Maier & Neustadt, L.L.P.

(57) ABSTRACT

An ultrasound diagnosis apparatus according to an embodiment includes a decomposing unit, a diffusion filter unit, an adjusting unit, and a reconstructing unit. The decomposing unit decomposes ultrasound image data into low-frequency and high-frequency decomposed image data at each of a predetermined number of levels, by a multi-resolution analysis. The diffusion filter unit applies a diffusion filter to the low-frequency and high-frequency decomposed image data at the lowest level and applies, at each of the levels other than the lowest, a diffusion filter to data output from the level immediately underneath and to the high-frequency decomposed image data, and also generates edge information for each of the levels. The adjusting unit adjusts a signal level of the high-frequency decomposed image data for each of the levels, based on the edge information. The reconstructing unit obtains corrected data of the ultrasound image data by performing a multi-resolution synthesis.

4 Claims, 10 Drawing Sheets

(51) Int. Cl.
*A61B 5/12* (2006.01)
*G01S 7/52* (2006.01)
*A61B 6/00* (2006.01)

(56) References Cited

U.S. PATENT DOCUMENTS

| | | | |
|---|---|---|---|
| 7,756,312 B2* | 7/2010 | Hsieh et al. | 382/128 |
| 8,202,221 B2* | 6/2012 | Osumi et al. | 600/443 |
| 2008/0317358 A1* | 12/2008 | Bressan et al. | 382/224 |
| 2009/0171208 A1* | 7/2009 | Osumi et al. | 600/443 |
| 2010/0228129 A1* | 9/2010 | Osumi | 600/443 |
| 2010/0286525 A1* | 11/2010 | Osumi | 600/443 |
| 2013/0077893 A1* | 3/2013 | Moon et al. | 382/299 |

FOREIGN PATENT DOCUMENTS

| | | |
|---|---|---|
| JP | 2009-153918 A | 7/2009 |
| JP | 2010-227554 A | 10/2010 |
| JP | 2010-259658 A | 11/2010 |

OTHER PUBLICATIONS

International Search Report mailed Jul. 31, 2012 for PCT/JP2012/066886 filed on Jul. 2, 2012 with English Translation.
International Written Opinion mailed Jul. 31, 2012 for PCT/JP2012/066886 filed on Jul. 2, 2012.

* cited by examiner

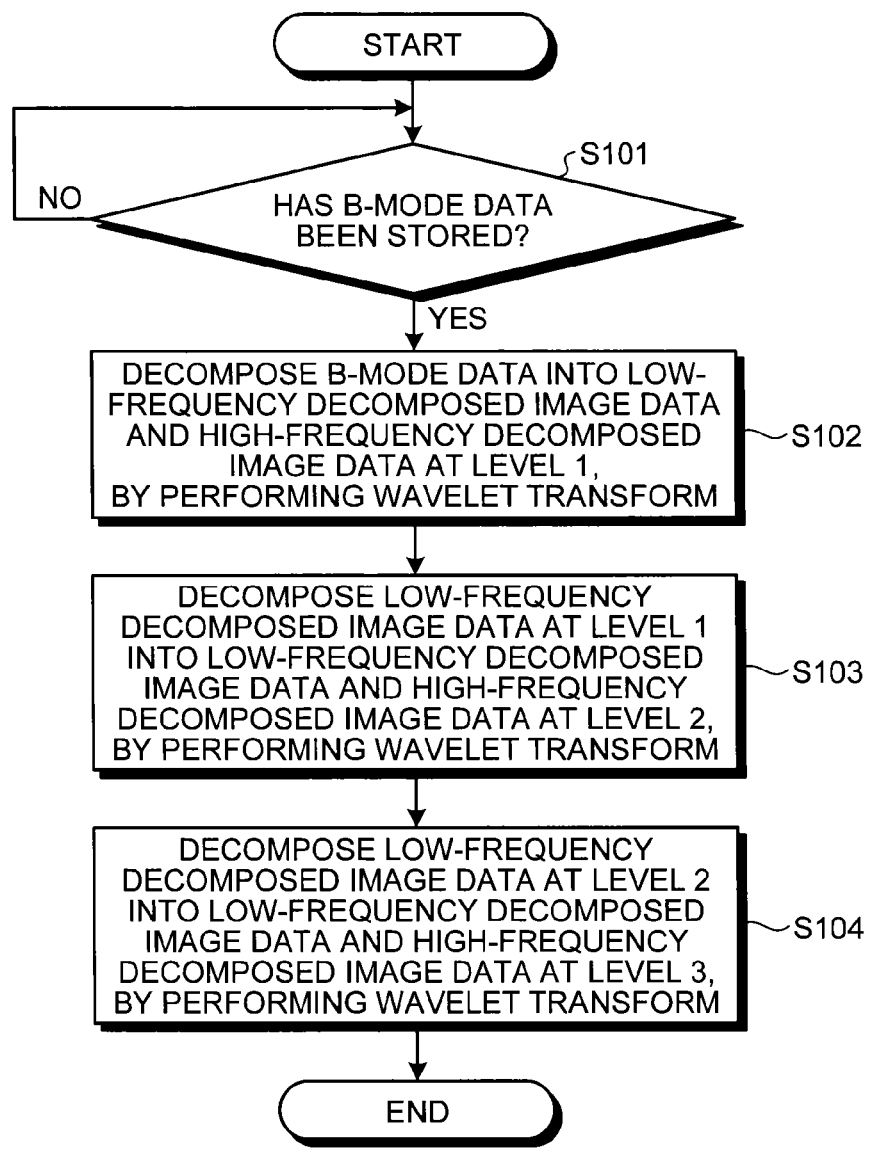

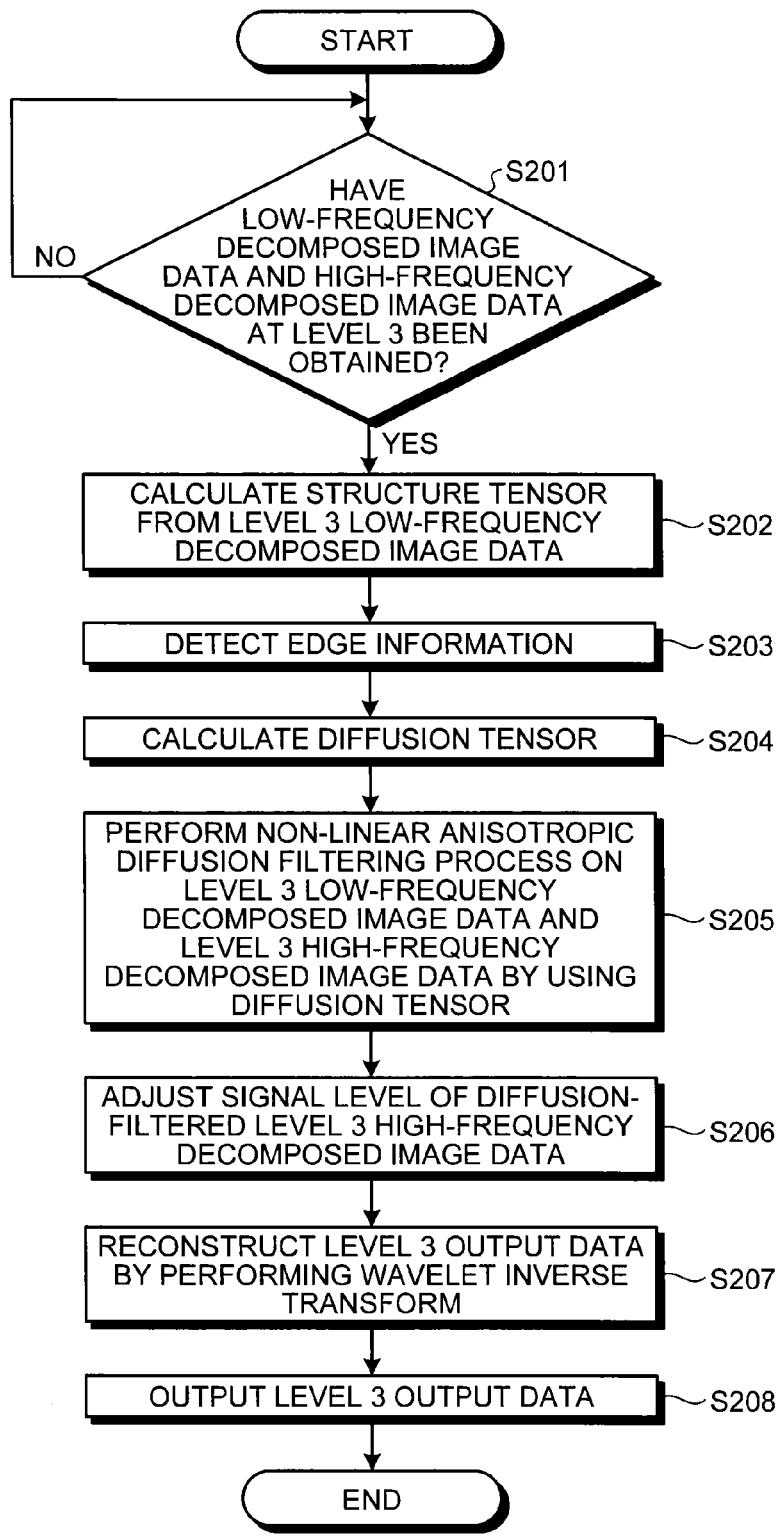

ULTRASOUND DIAGNOSIS APPARATUS, IMAGE PROCESSING APPARATUS, AND IMAGE PROCESSING METHOD

CROSS-REFERENCE TO RELATED APPLICATIONS

This application is a continuation of PCT international application Ser. No. PCT/JP2012/066886 filed on Jul. 2, 2012 which designates the United States, incorporated herein by reference, and which claims the benefit of priority from Japanese Patent Application No. 2011-146254, filed on Jun. 30, 2011, the entire contents of which are incorporated herein by reference.

FIELD

Embodiments described herein relate generally to an ultrasound diagnosis apparatus, an image processing apparatus, and an image processing method.

BACKGROUND

As a process to eliminate speckles occurring in an ultrasound image, a filtering process in which a multi-resolution analysis is combined with a non-linear anisotropic diffusion filter is conventionally known.

During a diffusion filtering process that uses a non-linear anisotropic diffusion filter, by applying mutually-different processes to an edge portion and to portions other than the edge portion, it is possible to obtain an image in which the edge is enhanced and from which speckles are eliminated. Further, when a multi-resolution analysis is performed, by sequentially performing processes from a broad-perspective process targeting a low-resolution image to a localized process targeting a high-resolution image, it is possible to perform the diffusion filtering process at a higher speed and more efficiently.

In other words, during the filtering process described above, the diffusion filtering process is applied either to the low-frequency image resulting from the multi-resolution decomposition or to the high-order multi-resolution decomposed image, which is the data output from the level immediately underneath. In this situation, the non-linear anisotropic diffusion filter has a function to enhance the edge. However, when the diffusion filtering process is performed on an image having a low spatial frequency, the structure in a broad perspective is to be enhanced. It is therefore difficult to apply a strong edge enhancement.

BRIEF DESCRIPTION OF THE DRAWINGS

FIG. 7 is a flowchart for explaining a process performed by a decomposing unit according to the present embodiment;

FIG. 8 is a flowchart for explaining a process performed at Level 3 by the image processing unit according to the present embodiment;

DETAILED DESCRIPTION

An ultrasound diagnosis apparatus according to an embodiment includes a decomposing unit, a diffusion filter unit, an adjusting unit, and a reconstructing unit. The decomposing unit is configured to decompose ultrasound image data into low-frequency decomposed image data and high-frequency decomposed image data at each of a predetermined number of hierarchical levels, by performing a hierarchical multi-resolution analysis. The diffusion filter unit is configured to apply, at a lowest hierarchical level of the predetermined number of hierarchical levels, a non-linear anisotropic diffusion filter to the low-frequency decomposed image data and the high-frequency decomposed image data at the lowest hierarchical level, configured to apply, at each of the hierarchical levels higher than the lowest hierarchical level, a non-linear anisotropic diffusion filter to data output from a hierarchical level immediately underneath that has been reconstructed by performing a multi-resolution analysis and to the high-frequency decomposed image data at that hierarchical level, and configured to generate, for each of the hierarchical levels, edge information of a signal either from the low-frequency decomposed image data at the lowest hierarchical level or from the data output from the hierarchical level immediately underneath. The adjusting unit is configured to adjust a signal level of the high-frequency decomposed image data for each of the hierarchical levels, based on the edge information obtained at each of the hierarchical levels. The reconstructing unit is configured to obtain corrected data of the ultrasound image data by hierarchically performing a multi-resolution synthesis on data output from the diffusion filter unit and data output from the adjusting unit that are obtained at each of the hierarchical levels.

In the following sections, exemplary embodiments of an ultrasound diagnosis apparatus will be explained in detail, with reference to the accompanying drawings.

Figure 1:
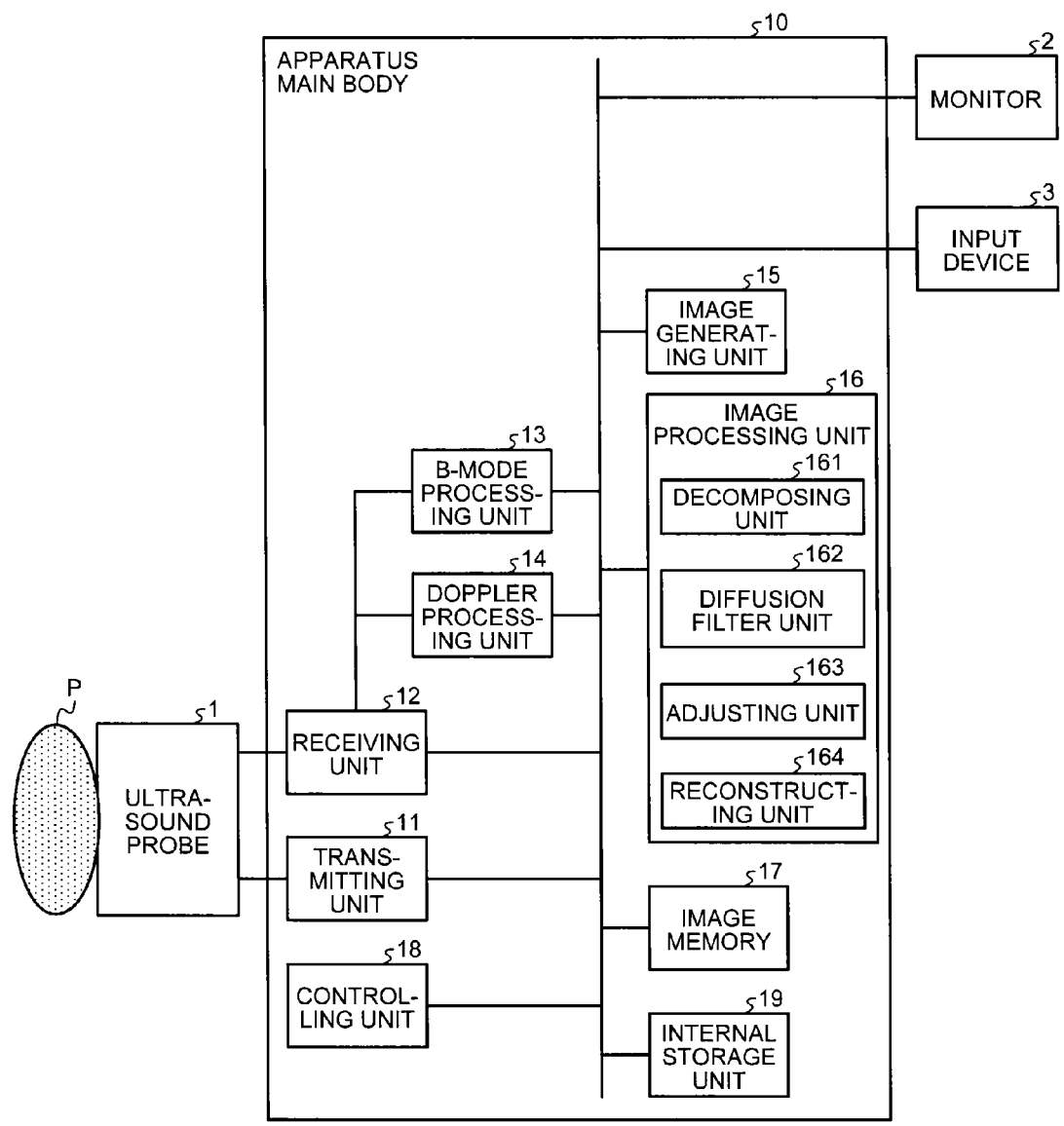
FIG. 1 is a drawing for explaining an exemplary configuration of an ultrasound diagnosis apparatus according to a present embodiment.

First, a configuration of an ultrasound diagnosis apparatus according to an exemplary embodiment will be explained. FIG. 1 is a drawing for explaining an exemplary configuration of the ultrasound diagnosis apparatus according to the present embodiment. As shown in FIG. 1, the ultrasound diagnosis apparatus according to the present embodiment includes an ultrasound probe 1, a monitor 2, an input device 3, and an apparatus main body 10.

The ultrasound probe 1 includes a plurality of piezoelectric transducer elements, which generate an ultrasound wave based on a drive signal supplied from a transmitting unit 11 included in the apparatus main body 10 (explained later). Further, the ultrasound probe 1 receives a reflected wave from a subject P and converts the received reflected wave into an electric signal. Further, the ultrasound probe 1 includes matching layers included in the piezoelectric transducer elements, as well as a backing material that prevents ultrasound waves from propagating rearward from the piezoelectric transducer elements. The ultrasound probe 1 is detachably connected to the apparatus main body 10.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift, depending on a velocity component of the moving object with respect to the ultrasound wave transmission direction.

It should be noted that the present embodiment is applicable to a situation where the ultrasound probe 1 is an ultrasound probe configured to scan the subject P two-dimensionally and to a situation where the ultrasound probe 1 is an ultrasound probe configured to scan the subject P three-dimensionally, while using the ultrasound waves. An example of the ultrasound probe 1 configured to scan the subject P three-dimensionally is a mechanical scan probe that scans the subject P three-dimensionally by causing a plurality of ultrasound transducer elements which scans the subject P two-dimensionally to swing at a predetermined angle (a swinging angle). Another example of the ultrasound probe 1 configured to scan the subject P three-dimensionally is a two-dimensional ultrasound probe (a 2D probe) that performs an ultrasound scan on the subject P three-dimensionally by using a plurality of ultrasound transducer elements that are arranged in a matrix formation. The 2D probe is also able to scan the subject P two-dimensionally by transmitting the ultrasound waves in a converged manner.

The input device 3 includes a mouse, a keyboard, a button, a panel switch, a touch command screen, a foot switch, a trackball, a joystick, and the like. The input device 3 receives various types of setting requests from an operator of the ultrasound diagnosis apparatus and transfers the received various types of setting requests to the apparatus main body 10.

The monitor 2 displays a Graphical User Interface (GUI) used by the operator of the ultrasound diagnosis apparatus to input the various types of setting requests through the input device 3 and displays an ultrasound image and the like generated by the apparatus main body 10.

The apparatus main body 10 is an apparatus that generates the ultrasound image based on the reflected wave received by the ultrasound probe 1. As shown in FIG. 1, the apparatus main body 10 includes the transmitting unit 11, a receiving unit 12, a B-mode processing unit 13, a Doppler processing unit 14, an image generating unit 15, an image processing unit 16, an image memory 17, a controlling unit 18, and an internal storage unit 19.

The transmitting unit 11 includes a trigger generating circuit, a transmission delaying circuit, a pulser circuit, and the like and supplies the drive signal to the ultrasound probe 1. The pulser circuit repeatedly generates a rate pulse for forming a transmission ultrasound wave at a predetermined rate frequency. The transmission delaying circuit applies a delay time that is required to converge the ultrasound wave generated by the ultrasound probe 1 into the form of a beam and to determine transmission directionality and that corresponds to each of the piezoelectric transducer elements, to each of the rate pulses generated by the pulser circuit. Further, the trigger generating circuit applies a drive signal (a drive pulse) to the ultrasound probe 1 with timing based on the rate pulses. In other words, the transmission delaying circuit arbitrarily adjusts the directions of the transmissions from the surface of the piezoelectric transducer element, by varying the delay time applied to the rate pulses.

The transmitting unit 11 has a function to be able to instantly change the transmission frequency, the transmission drive voltage, and the like, for the purpose of executing a predetermined scanning sequence based on an instruction from the controlling unit 18 (explained later). In particular, the configuration to change the transmission drive voltage is realized by using a linear-amplifier-type transmitting circuit of which the value can be instantly switched or by using a mechanism configured to electrically switch between a plurality of power source units.

The receiving unit 12 includes an amplifier circuit, an Analog/Digital (A/D) converter, an adder, and the like and generates reflected-wave data by performing various types of processes on the reflected-wave signal received by the ultrasound probe 1. The amplifier circuit amplifies the reflected-wave signal for each of channels and performs a gain correcting process thereon. The A/D converter applies an A/D conversion to the gain-corrected reflected-wave signal and applies a delay time required to determine reception directionality to digital data. The adder generates the reflected-wave data by performing an adding process on the reflected-wave signals processed by the A/D converter. As a result of the adding process performed by the adder, reflected components from the direction corresponding to the reception directionality of the reflected-wave signal are emphasized.

In this manner, the transmitting unit 11 and the receiving unit 12 control the transmission directionality and the reception directionality in the transmission and the reception of the ultrasound wave.

In this situation, if the ultrasound probe 1 is configured to be able to perform a three-dimensional scan, the transmitting unit 11 and the receiving unit 12 are each able to also cause a three-dimensional ultrasound beam to be transmitted from the ultrasound probe 1 to the subject P, so that three-dimensional reflected-wave data is generated from three-dimensional reflected-wave signals received by the ultrasound probe 1.

The B-mode processing unit 13 receives the reflected-wave data from the receiving unit 12 and generates data (B-mode data) in which the strength of each signal is expressed by a degree of brightness, by performing a logarithmic amplification, an envelope detection process, and the like on the received reflected-wave data.

The Doppler processing unit 14 extracts bloodstreams, tissues, and contrast echo components under the influence of the Doppler effect by performing a frequency analysis so as to obtain velocity information from the reflected-wave data received from the receiving unit 12, and further generates data (Doppler data) obtained by extracting moving object information such as an average velocity, the dispersion, the power, and the like for a plurality of points.

The B-mode processing unit 13 and the Doppler processing unit 14 according to the present embodiment are able to process both two-dimensional reflected-wave data and three-dimensional reflected-wave data. In other words, the B-mode processing unit 13 is able to generate two-dimensional B-mode data from two-dimensional reflected-wave data and is also able to generate three-dimensional B-mode data from three-dimensional reflected-wave data. The Doppler processing unit 14 is able to generate two-dimensional Doppler data from two-dimensional reflected-wave data and is also able to generate three-dimensional Doppler data from three-dimensional reflected-wave data.

The image generating unit 15 generates ultrasound image data based on the reflected wave received by the ultrasound probe 1. In other words, the image generating unit 15 generates the ultrasound image data to be output to the monitor 2, from the data generated by the B-mode processing unit 13 and the Doppler processing unit 14. More specifically, from the two-dimensional B-mode data generated by the B-mode processing unit 13, the image generating unit 15 generates B-mode image data in which the strength of the reflected wave is expressed by a degree of brightness. Further, from the two-dimensional Doppler data generated by the Doppler processing unit 14, the image generating unit 15 generates an average velocity image, a dispersion image, and a power image, expressing the moving object information, or Doppler image data, which is an image combining these images.

In this situation, generally, the image generating unit 15 converts (by performing a scan convert process) a scanning line signal sequence from an ultrasound scan into a scanning line signal sequence in a video format used by, for example, television and generates display-purpose ultrasound image data. More specifically, the image generating unit 15 generates the display-purpose ultrasound image data by performing a coordinate transformation process compliant with the ultrasound scanning form by the ultrasound probe 1. Further, the image generating unit 15 synthesizes text information of various parameters, scale graduations, body marks, and the like with the display-purpose ultrasound image data.

In other words, the B-mode data and the Doppler data are the ultrasound image data before the scan convert process is performed. The data generated by the image generating unit 15 is the display-purpose ultrasound image data obtained after the scan convert process is performed. The B-mode data and the Doppler data may be referred to as raw data.

Further, the image generating unit 15 is also able to generate three-dimensional ultrasound image data. In other words, the image generating unit 15 is also able to generate three-dimensional B-mode image data by performing a coordinate transformation process on the three-dimensional B-mode data generated by the B-mode processing unit 13. The image generating unit 15 is also able to generate three-dimensional color Doppler image data by performing a coordinate transformation process on the three-dimensional Doppler data generated by the Doppler processing unit 14.

Further, the image generating unit 15 is also able to perform various types of rendering processes on three-dimensional ultrasound image data (volume data). More specifically, the image generating unit 15 is able to generate display-purpose two-dimensional ultrasound image data by performing a rendering process on three-dimensional ultrasound image data. An example of the rendering process performed by the image generating unit 15 is a process to reconstruct a Multi Planar Reconstruction (MPR) image by implementing an MPR method. Another example of the rendering process performed by the image generating unit 15 is a Volume Rendering (VR) process to generate a two-dimensional image in which three-dimensional information is reflected.

The image processing unit 16 is a processing unit that performs various types of image processing on the ultrasound image data. In the present embodiment, the image processing unit 16 performs processes to eliminate speckles and to enhance the edge on the ultrasound image data.

To serve as a processing unit that performs such processes, the image processing unit 16 includes a decomposing unit 161, a diffusion filter unit 162, an adjusting unit 163, and a reconstructing unit 164, as shown in FIG. 1. The decomposing unit 161 is a processing unit that decomposes image data into low-frequency decomposed image data and high-frequency decomposed image data by performing a multi-resolution analysis. The diffusion filter unit 162 is a processing unit that detects edge information from image data and applies a non-linear anisotropic diffusion filter based on the detected edge information. The adjusting unit 163 is a processing unit that adjusts a signal level of the image data. The reconstructing unit 164 is a processing unit that performs a reconstructing process to synthesize together low-frequency decomposed image data and high-frequency decomposed image data by performing a multi-resolution analysis.

In the present embodiment, an example will be explained in which the decomposing unit 161 performs a wavelet transform as a decomposing process realized by the multi-resolution analysis, whereas the reconstructing unit 164 performs a wavelet inverse transform as a synthesizing process (a reconstructing process) realized by the multi-resolution analysis. It should be noted, however, that the present embodiment is also applicable to the situation where the decomposing unit 161 and the reconstructing unit 164 perform a multi-resolution decomposition and a multi-resolution synthesis by implementing a Laplacian pyramid method.

Further, the ultrasound image data used as a processing target by the image processing unit 16 may be the raw data generated by the B-mode processing unit 13 and the Doppler processing unit 14 or may be the display-purpose ultrasound image data generated by the image generating unit 15. Processes performed by the image processing unit 16 according to the present embodiment will be explained later.

The image memory 17 is a memory for storing therein the ultrasound image data generated by the image generating unit 15 and processing results of the image processing unit 16. Further, the image memory 17 is also able to store therein the raw data generated by the B-mode processing unit 13 and the Doppler processing unit 14.

The internal storage unit 19 stores therein various types of data such as a control program to realize ultrasound transmissions and receptions, image processing, and display processing, as well as diagnosis information (e.g., patients' IDs, medical doctors' observations), diagnosis protocols, and various types of body marks. Further, the internal storage unit 19 may be used, as necessary, for storing therein any of the images stored in the image memory 17. Furthermore, the data stored in the internal storage unit 19 can be transferred to any external peripheral device via an interface circuit (not shown).

The controlling unit 18 is a controlling processor (a Central Processing Unit (CPU)) that realizes functions of an information processing apparatus and is configured to control the entire processes performed by the ultrasound diagnosis apparatus. More specifically, based on the various types of setting requests input by the operator via the input device 3 and various types of control programs and various types of data read from the internal storage unit 19, the controlling unit 18 controls processes performed by the transmitting unit 11, the receiving unit 12, the B-mode processing unit 13, the Doppler processing unit 14, the image generating unit 15, and the image processing unit 16.

Further, the controlling unit 18 exercises control so that the monitor 2 displays the ultrasound image data stored in the image memory 17 and various types of image data stored in the internal storage unit 19, or a GUI used for realizing the processes performed by the image processing unit 16 and the processing results of the image processing unit 16, and the like.

An overall configuration of the ultrasound diagnosis apparatus according to the present embodiment has thus been explained. The ultrasound diagnosis apparatus according to the present embodiment configured as described above captures an ultrasound image by performing an ultrasound transmission and reception. In this situation, when reflecting objects of which the size is very much smaller than the wavelength of the transmitted ultrasound wave are densely present, the reflected-wave signals interfere with one another. The magnitude of the interference is represented by a magnitude of the amplitude of the reflected-wave signal. As a result, dot-like artifacts (speckles) occur in an ultrasound image depicting such amplitude information.

Such speckles hinder an accurate visual perception of the position of a border between living tissues or the shape of living tissues. For this reason, various types of processes to eliminate speckles have conventionally been performed. For example, according to a speckle eliminating method that uses a multi-resolution analysis (MRA), a multi-resolution decomposition is performed on ultrasound image data, so that threshold processing or a weighting process is performed on high-frequency components of the decomposed image at each of the different levels. As a result, the speckles are eliminated; however, ultrasound images obtained by displaying ultrasound image data processed in such a manner may seem artificial to viewers.

As another example, according to a speckle eliminating method that uses a non-linear anisotropic diffusion filter, mutually-different processes are applied to an edge portion (a border potion between tissues) and to portions other than the edge portion. As a result, it is possible to obtain an image in which the edge is enhanced and from which the speckles are eliminated. However, because the non-linear anisotropic diffusion filter requires a calculation process to obtain a solution of a partial differential equation, the computing process takes time. In addition, when the process using the non-linear anisotropic diffusion filter is performed alone, although a certain degree of speckle reducing effect is achieved, the level of speckle eliminating effect may not be sufficiently high.

To cope with this situation, in recent years, a speckle eliminating method has been developed by which a filtering process is performed by combining a multi-resolution analysis with a non-linear anisotropic diffusion filter. In the following sections, the speckle eliminating method by which the filtering process is performed by combining a multi-resolution analysis with a non-linear anisotropic diffusion filter will be referred to as "the conventional method".

According to the conventional method, for example, ultrasound image data is multi-resolution decomposed into low-frequency decomposed image data and high-frequency decomposed image data at a predetermined number of hierarchical levels (predetermined multiple levels), by performing a wavelet transform. Further, according to the conventional method, processes using non-linear anisotropic diffusion filters are sequentially performed from the image data in a lower level to the image data in an upper level.

Figure 2:
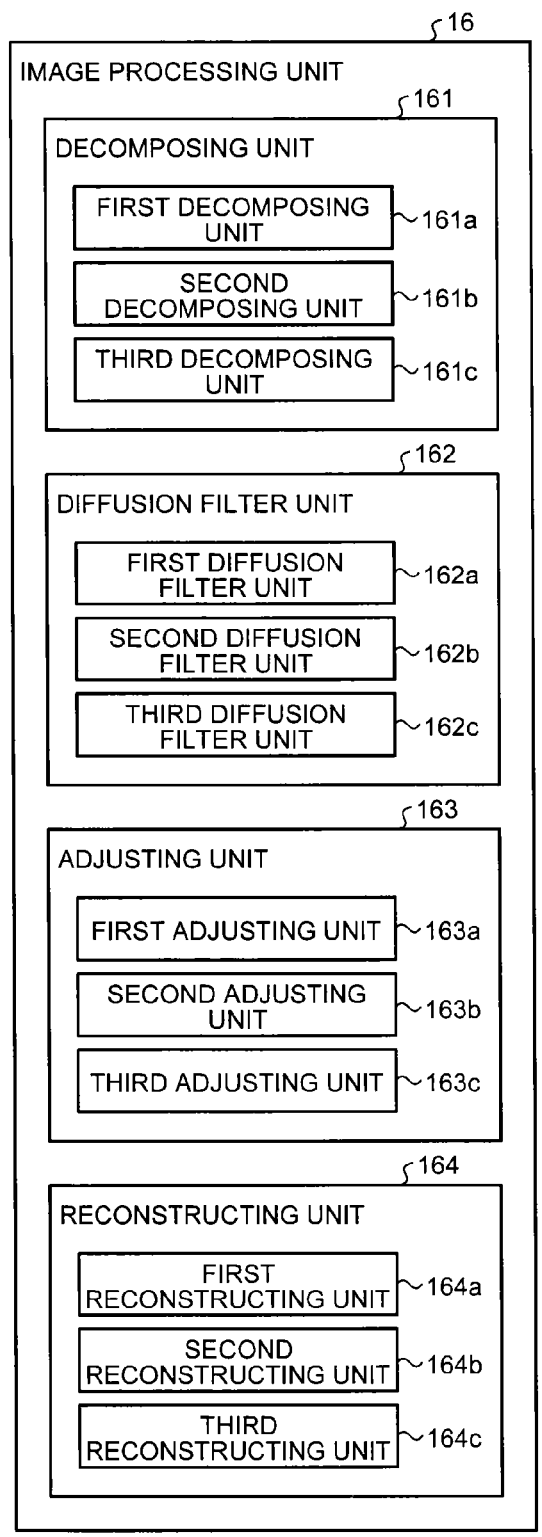
FIG. 2 is a drawing for explaining an exemplary functional configuration of an image processing unit in a situation where the number of levels is set to "3"

Next, an example in which the image processing unit 16 illustrated in FIG. 1 implements the conventional method will be explained. For example, if the number of levels in the multi-resolution decomposition is "3", the decomposing unit 161, the diffusion filter unit 162, the adjusting unit 163, and the reconstructing unit 164 included in the image processing unit 16 illustrated in FIG. 1 have a functional configuration illustrated in FIG. 2, under the control of the controlling unit 18. FIG. 2 is a drawing for explaining the exemplary functional configuration of the image processing unit in the situation where the number of levels is set to "3".

When the number of levels is set to "3", the decomposing unit 161 is configured as three functional processing units that are namely a first decomposing unit 161a, a second decomposing unit 161b, and a third decomposing unit 161c, as shown in FIG. 2, so as to perform processes at Level 1, Level 2, and Level 3, respectively. Further, the diffusion filter unit 162 is configured as three functional processing units that are namely a first diffusion filter unit 162a, a second diffusion filter unit 162b, and a third diffusion filter unit 162c, as shown in FIG. 2, so as to perform processes at Level 1, Level 2, and Level 3, respectively.

In addition, the adjusting unit 163 is configured as three functional processing units that are namely a first adjusting unit 163a, a second adjusting unit 163b, and a third adjusting unit 163c, as shown in FIG. 2, so as to perform processes at Level 1, Level 2, and Level 3, respectively. Furthermore, the reconstructing unit 164 is configured as three functional processing units that are namely a first reconstructing unit 164a, a second reconstructing unit 164b, and a third reconstructing unit 164c, as shown in FIG. 2, so as to perform processes at Level 1, Level 2, and Level 3, respectively.

Figure 3:
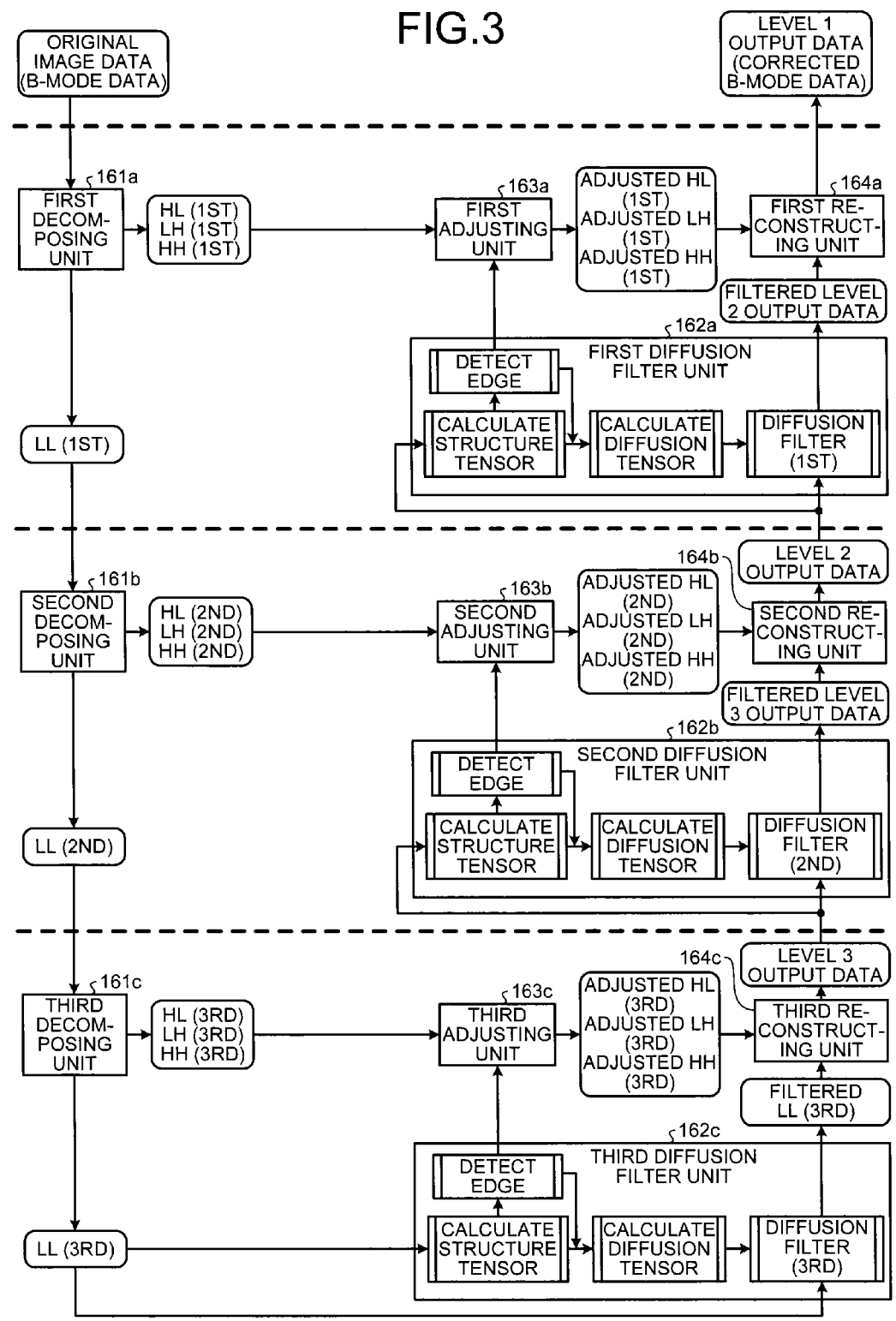
FIG. 3 is a drawing for explaining a conventional method.

FIG. 3 is a drawing for explaining the conventional method. In one example illustrated in FIG. 3, original image data used by the image processing unit 16 as a processing target is B-mode data generated by the B-mode processing unit 13.

The first decomposing unit 161a decomposes the B-mode data into low-frequency decomposed image data and high-frequency decomposed image data by performing a multi-resolution analysis. More specifically, by performing a wavelet transform (a discrete wavelet transform), the first decomposing unit 161a decomposes the B-mode data into "LL", which is a piece of low-frequency decomposed image data, and "HL, LH, and HH", which are pieces of high-frequency decomposed image data. In this situation, "LL" is a piece of image data in which the components in both the horizontal direction and the vertical direction are low-frequency components. "HL" is a piece of image data in which the component in the horizontal direction is a high-frequency component, whereas the component in the vertical direction is a low-frequency component. "LH" is a piece of image data in which the component in the horizontal direction is a low-frequency component, whereas the component in the vertical direction is a high-frequency component. "HH" is a piece of image data in which the components in both the horizontal direction and the vertical direction are high-frequency components.

As shown in FIG. 3, the first decomposing unit 161a outputs "LL(first)" (hereinafter, "LL(1st)"), which is LL at Level 1, to the second decomposing unit 161b and outputs "HL(1st), LH(1st), and HH(1st)", which are HL, LH, and HH at Level 1, to the first adjusting unit 163a.

The second decomposing unit 161b decomposes LL(1st) into low-frequency decomposed image data and high-frequency decomposed image data. In other words, as shown in FIG. 3, the second decomposing unit 161b decomposes LL(1st) into "LL(second)" (hereinafter, "LL(2nd)"), which is a piece of low-frequency decomposed image data at Level 2 and "HL(2nd), LH(2nd), and HH(2nd)", which are pieces of high-frequency decomposed image data at Level 2. Further, as shown in FIG. 3, the second decomposing unit 161b outputs "LL(2nd)" to the third decomposing unit 161c and outputs "HL(2nd), LH(2nd), and HH(2nd)" to the second adjusting unit 163b.

The third decomposing unit 161c decomposes LL(2nd) into low-frequency decomposed image data and high-frequency decomposed image data. In other words, as shown in FIG. 3, the third decomposing unit 161c decomposes LL(2nd) into "LL(third)" (hereinafter, "LL(3rd)"), which is a piece of low-frequency decomposed image data at Level 3 and "HL(3rd), LH(3rd), and HH(3rd)", which are pieces of high-frequency decomposed image data at Level 3. Further, as shown in FIG. 3, the third decomposing unit 161c outputs "LL(3rd)" to the third diffusion filter unit 162c and outputs "HL(3rd), LH(3rd), and HH(3rd)" to the third adjusting unit 163c.

As a result of the multi-resolution decomposition, the decomposed image data has half the dimensions lengthwise and widthwise, compared to the dimensions prior to the decomposition. In other words, the resolution of the image data at Level 1 is "(½)×(½)=¼" of the resolution of the B-mode data; the resolution of the image data at Level 2 is "(¼)×(¼)=1/16" of the resolution of the B-mode data; and the resolution of the image data at Level 3 is "(⅛)×(⅛)=1/64" of the resolution of the B-mode data.

After the multi-resolution decomposition is performed, the processes are performed in the order of Level 3, Level 2, and Level 1. As shown in FIG. 3, the third diffusion filter unit 162c calculates a structure tensor by using "LL(3rd)" and detects information ("edge information") related to the edge of "LL(3rd)" from the structure tensor. After that, as shown in FIG. 3, the third diffusion filter unit 162c calculates a diffusion tensor from the structure tensor and the edge information and applies a non-linear anisotropic diffusion filter (3rd) to "LL(3rd)" by using the calculated diffusion tensor. Subsequently, as shown in FIG. 3, the third diffusion filter unit 162c outputs "filtered LL(3rd)" to the third reconstructing unit 164c.

Further, as shown in FIG. 3, the third adjusting unit 163c adjusts signal levels of "HL(3rd), LH(3rd), and HH(3rd)" by using the edge information detected by the third diffusion filter unit 162c. After that, as shown in FIG. 3, the third adjusting unit 163c outputs "adjusted HL(3rd), adjusted LH(3rd), and adjusted HH(3rd)" to the third reconstructing unit 164c.

As shown in FIG. 3, the third reconstructing unit 164c reconstructs "filtered LL(3rd)" and "adjusted HL(3rd), adjusted LH(3rd), and adjusted HH(3rd)" by performing a multi-resolution synthesis. More specifically, by performing a wavelet inverse transform, the third reconstructing unit 164c synthesizes together "filtered LL(3rd)" and "adjusted HL(3rd), adjusted LH(3rd), and adjusted HH(3rd)". After that, as shown in FIG. 3, the third reconstructing unit 164c outputs "Level 3 output data", which is the data resulting from the reconstruction, to the second diffusion filter unit 162b at Level 2. As a result of the process performed by the third reconstructing unit 164c, the resolution of the "Level 3 output data" is "1/16" of the resolution of the B-mode data.

At Level 2, as shown in FIG. 3, the second diffusion filter unit 162b calculates a structure tensor by using the "Level 3 output data" and detects edge information of the "Level 3 output data" from the structure tensor. After that, as shown in FIG. 3, the second diffusion filter unit 162b calculates a diffusion tensor from the structure tensor and the edge information and applies a non-linear anisotropic diffusion filter (2nd) to the "Level 3 output data" by using the calculated diffusion tensor. Subsequently, as shown in FIG. 3, the second diffusion filter unit 162b outputs "filtered Level 3 output data" to the second reconstructing unit 164b.

Further, as shown in FIG. 3, the second adjusting unit 163b adjusts signal levels of "HL(2nd), LH(2nd), and HH(2nd)" by using the edge information detected by the second diffusion filter unit 162b. After that, as shown in FIG. 3, the second adjusting unit 163b outputs "adjusted HL(2nd), adjusted LH(2nd), and adjusted HH(2nd)" to the second reconstructing unit 164b.

As shown in FIG. 3, by performing a wavelet inverse transform, the second reconstructing unit 164b synthesizes together "filtered Level 3 output data" and "adjusted HL(2nd), adjusted LH(2nd), and adjusted HH(2nd)". After that, as shown in FIG. 3, the second reconstructing unit 164b outputs "Level 2 output data", which is the data resulting from the reconstruction, to the first diffusion filter unit 162a at Level 1. As a result of the process performed by the second reconstructing unit 164b, the resolution of the "Level 2 output data" is "¼" of the resolution of the B-mode data.

At Level 1, as shown in FIG. 3, the first diffusion filter unit 162a calculates a structure tensor by using the "Level 2 output data" and detects edge information of the "Level 2 output data" from the structure tensor. After that, as shown in FIG. 3, the first diffusion filter unit 162a calculates a diffusion tensor from the structure tensor and the edge information and applies a non-linear anisotropic diffusion filter (1st) to the "Level 2 output data" by using the calculated diffusion tensor. Subsequently, as shown in FIG. 3, the first diffusion filter unit 162a outputs "filtered Level 2 output data" to the first reconstructing unit 164a.

Further, as shown in FIG. 3, the first adjusting unit 163a adjusts signal levels of "HL(1st), LH(1st), and HH(1st)" by using the edge information detected by the first diffusion filter unit 162a. After that, as shown in FIG. 3, the first adjusting unit 163a outputs "adjusted HL(1st), adjusted LH(1st), and adjusted HH(1st)" to the first reconstructing unit 164a.

As shown in FIG. 3, by performing a wavelet inverse transform, the first reconstructing unit 164a synthesizes together "filtered Level 2 output data" and "adjusted HL(1st), adjusted LH(1st), and adjusted HH(1st)". After that, as shown in FIG. 3, the first reconstructing unit 164a outputs "Level 1 output data", which is the data resulting from the reconstruction. More specifically, the first reconstructing unit 164a outputs the "Level 1 output data" to the image generating unit 15 as "corrected B-mode data". As a result of the process performed by the first reconstructing unit 164a, the resolution of the "Level 1 output data" is equal to the resolution of the B-mode data. By performing a scan convert process on the corrected B-mode data, the image generating unit 15 generates display-purpose ultrasound image data.

As explained above, according to the conventional method illustrated in FIG. 3, the diffusion filtering process is applied either to the low-frequency decomposed image data resulting from the multi-resolution decomposition or to the higher-order multi-resolution decomposed image, which is the data output from the level immediately underneath. As a result, according to the conventional method, it is possible to perform the diffusion filtering process at a high speed and efficiently. Further, due to a synergistic effect of the multi-resolution analysis and the non-linear anisotropic diffusion filtering process, it is possible to eliminate the speckles precisely.

Figure 4A:
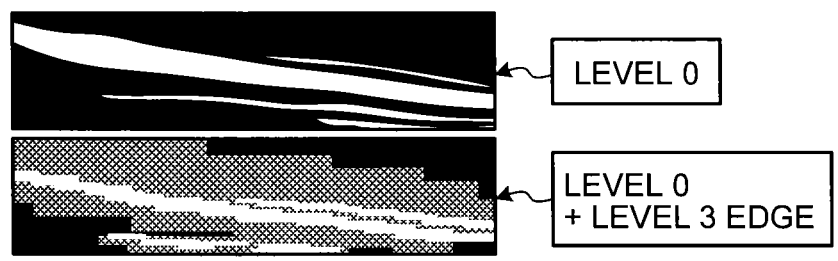
FIG. 4A and FIG. 4B are drawings for explaining the problem of the conventional method.
Figure 4B:

However, according to the conventional method described above, because the edge enhancing process using the non-linear anisotropic diffusion filter is performed also on the image having a low spatial frequency such as LL(3rd), for example, the structure in a broad perspective is enhanced, which is not desirable. For instance, when a strong edge enhancement is applied according to the conventional method described above, a diagonal structure is enhanced so as to seem like a stair-stepped structure. FIGS. 4A and 4B are drawings for explaining the problem of the conventional method.

As explained above, the resolution of the image data at Level 3 is "1/64" of the resolution of the B-mode data. For this reason, for example, if the edge detection result at Level 3 (see the area with grid hatching in the drawing) is superimposed while being enlarged to the number of pixels of the B-mode data (Level 0) as shown in FIG. 4A, the edge portion of the diagonal structure becomes stair-stepped. As a result, when a strong edge enhancement is applied at each of the levels, a diagonal structure rendered in the ultrasound image displayed on the monitor 2 will have a stair-stepped form and not the real form, as shown in FIG. 4B. Consequently, the result of the edge enhancement rendered in the ultrasound image generated according to the conventional method makes the viewer feel that something is wrong with the ultrasound image, in some situations.

To cope with these situations, the decomposing unit 161, the diffusion filter unit 162, the adjusting unit 163, and the reconstructing unit 164 included in the image processing unit 16 according to the present embodiment performs processes as described below, to generate an ultrasound image in which the edge is enhanced without causing the feeling that something is wrong with the ultrasound image and from which speckles are eliminated.

The decomposing unit 161 according to the present embodiment decomposes ultrasound image data into low-frequency decomposed image data and high-frequency decomposed image data at each of a predetermined number of hierarchical levels, by performing a hierarchical multi-resolution analysis.

Further, at the lowest hierarchical level of the predetermined number of hierarchical levels, the diffusion filter unit 162 according to the present embodiment applies a non-linear anisotropic diffusion filter to the low-frequency decomposed image data and the high-frequency decomposed image data at the lowest hierarchical level. Further, at each of the hierarchical levels higher than the lower hierarchical level, the diffusion filter unit 162 according to the present embodiment applies a non-linear anisotropic diffusion filter to the data output from the hierarchical level immediately underneath that has been reconstructed by performing a multi-resolution analysis and to the high-frequency decomposed image data at that hierarchical level. Further, in addition to applying the non-linear anisotropic diffusion filter, the diffusion filter unit 162 according to the present embodiment generates (detects), for each of the hierarchical levels, edge information of the signal either from the low-frequency decomposed image data at the lower hierarchical level or from the data output from the hierarchical level immediately underneath.

Further, based on the edge information obtained at each of the hierarchical levels, the adjusting unit 163 according to the present embodiment adjusts the signal level of the high-frequency decomposed image data for each of the hierarchical levels. More specifically, the adjusting unit 163 according to the present embodiment adjusts the signal level of the high-frequency decomposed image data to which the non-linear anisotropic diffusion filter was applied, based on the edge information detected by the diffusion filter unit 162 when performing the non-linear anisotropic diffusion filtering process on the same hierarchical level as the hierarchical level of the high-frequency decomposed image data. Even more specifically, at the lowest hierarchical level, the adjusting unit 163 according to the present embodiment adjusts the signal level of the high-frequency decomposed image data to which the non-linear anisotropic diffusion filter was applied, based on the edge information detected by the diffusion filter unit 162 from the low-frequency decomposed image data at the lowest hierarchical level. In contrast, at each of the hierarchical levels higher than the lowest hierarchical level, the adjusting unit 163 according to the present embodiment adjusts the signal level of the high-frequency decomposed image data to which the non-linear anisotropic diffusion filter was applied, based on the edge information detected by the diffusion filter unit 162 from the data output from the hierarchical level immediately underneath.

Further, the reconstructing unit 164 according to the present embodiment obtains corrected data of the ultrasound image data by hierarchically performing a multi-resolution synthesis on the data output from the diffusion filter unit 162 and the data output from the adjusting unit 163 that are obtained at each of the hierarchical levels. More specifically, the reconstructing unit 164 according to the present embodiment reconstructs the data by performing the multi-resolution analysis, from the data that has been processed by the diffusion filter unit 162 and was not used in the process performed by the adjusting unit 163 and the data that has been processed by the adjusting unit 163 at the same hierarchical level as such data. After that, at each of the hierarchical levels lower than the highest hierarchical level of the predetermined number of hierarchical levels, the reconstructing unit 164 according to the present embodiment outputs the reconstructed data as the output data to be processed by the diffusion filter unit 162 at the hierarchical level immediately above. In contrast, at the highest hierarchical level, the reconstructing unit 164 according to the present embodiment outputs the reconstructed data as corrected data of the ultrasound image data.

More specifically, at the lowest hierarchical level, the diffusion filter unit 162 according to the present embodiment applies the non-linear anisotropic diffusion filter to the high-frequency decomposed image data at the lowest hierarchical level by using a diffusion filter coefficient calculated based on a structure tensor and edge information detected from the low-frequency decomposed image data at the lowest hierarchical level. In contrast, at each of the hierarchical levels higher than the lowest hierarchical level, the diffusion filter unit 162 according to the present embodiment applies the non-linear anisotropic diffusion filter to the high-frequency decomposed image data at that hierarchical level by using a diffusion filter coefficient calculated based on a structure tensor and edge information detected from the output data that was output by the reconstructing unit at the hierarchical level immediately underneath.

Figure 5:
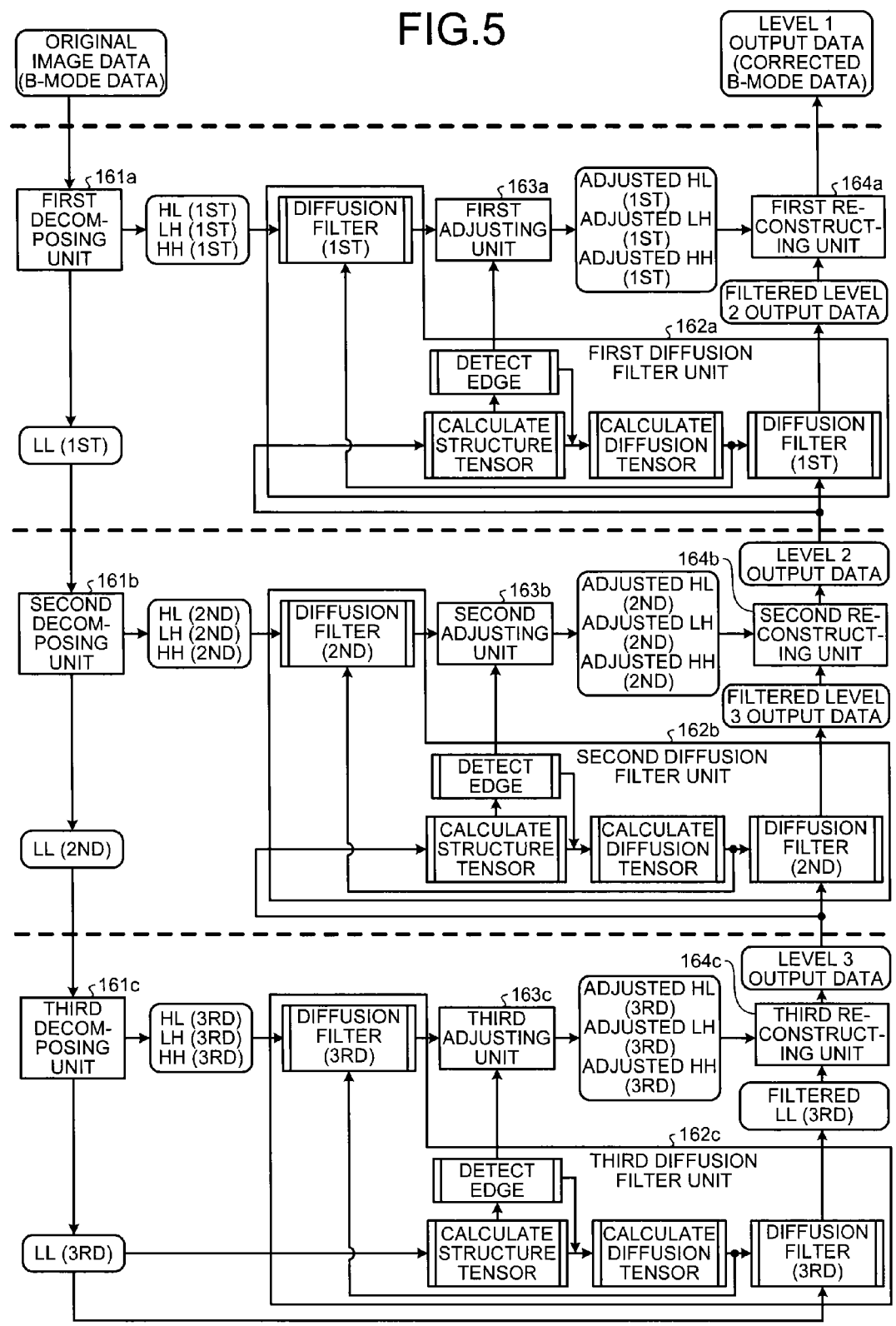
FIG. 5 is a drawing for explaining a speckle eliminating process performed by the image processing unit according to the present embodiment.

Next, processes performed by the decomposing unit 161, the diffusion filter unit 162, the adjusting unit 163, and the reconstructing unit 164 according to the present embodiment will be explained with reference to FIG. 5, by using an example in which the number of hierarchical levels (the number of levels) is set to "3", and the ultrasound image data serving as a processing target is B-mode data. FIG. 5 is a drawing for explaining a speckle eliminating process performed by the image processing unit according to the present embodiment.

To make the differences from the conventional method clear, the present embodiment will be explained while using the same reference characters as those of the processing units used in the explanation of the conventional method above. In other words, when the number of levels is set to "3", the decomposing unit 161, the diffusion filter unit 162, the adjusting unit 163, and the reconstructing unit 164 are each configured as the three functional processing units as shown in FIG. 2, so as to perform the processes at Level 1, Level 2, and Level 3, respectively.

First, as shown in FIG. 5, by performing a wavelet transform (a discrete wavelet transform), the first decomposing unit 161*a* decomposes the B-mode data into "LL (1st)", which is a piece of low-frequency decomposed image data, and "HL(1st), LH(1st), and HH(1st)", which are pieces of high-frequency decomposed image data. After that, as shown in FIG. 5, the first decomposing unit 161*a* outputs "LL(1st)" to the second decomposing unit 161*b*. Also, as shown in FIG. 5, the first decomposing unit 161*a* outputs "HL(1st), LH(1st), and HH(1st)", to the first diffusion filter unit 162*a*.

As shown in FIG. 5, the second decomposing unit 161*b* decomposes LL(1st) into "LL(2nd)" and "HL(2nd), LH(2nd), and HH(2nd)". After that, as shown in FIG. 5, the second decomposing unit 161*b* outputs "LL(2nd)" to the third decomposing unit 161*c*. Also, as shown in FIG. 5, the second decomposing unit 161*b* outputs "HL(2nd), LH(2nd), and HH(2nd)", to the second diffusion filter unit 162*b*.

As shown in FIG. 5, the third decomposing unit 161*c* decomposes LL(2nd) into "LL(3rd)" and "HL(3rd), LH(3rd), and HH(3rd)". After that, as shown in FIG. 5, the third decomposing unit 161*c* outputs "LL(3rd)" and "HL(3rd), LH(3rd), and HH(3rd)" to the third diffusion filter unit 162*c*.

After the multi-resolution decomposition is performed, the processes are performed in the order of Level 3, Level 2, and Level 1. As shown in FIG. 5, the third diffusion filter unit 162*c* calculates a structure tensor by using "LL(3rd)" and detects edge information of "LL(3rd)" from the structure tensor. After that, as shown in FIG. 5, the third diffusion filter unit 162*c* calculates a diffusion tensor from the structure tensor and the edge information and applies a non-linear anisotropic diffusion filter (3rd) to "LL(3rd)" by using the calculated diffusion tensor. Subsequently, as shown in FIG. 5, the third diffusion filter unit 162*c* outputs "filtered LL(3rd)" to the third reconstructing unit 164*c*.

Further, as shown in FIG. 5, the third diffusion filter unit 162*c* applies a non-linear anisotropic diffusion filter (3rd) to "HL(3rd), LH(3rd), and HH(3rd)" by using a diffusion filter coefficient of the diffusion tensor calculated from "LL(3rd)" and outputs the result to the third adjusting unit 163*c*.

As shown in FIG. 5, the third adjusting unit 163*c* adjusts signal levels of "diffusion-filtered HL(3rd), diffusion-filtered LH(3rd), and diffusion-filtered HH(3rd)" on which the diffusion filtering process was performed, by using the edge information detected by the third diffusion filter unit 162*c*. After that, as shown in FIG. 5, the third adjusting unit 163*c* outputs "adjusted HL(3rd), adjusted LH(3rd), and adjusted HH(3rd)" to the third reconstructing unit 164*c*.

As shown in FIG. 5, the third reconstructing unit 164*c* synthesizes together "filtered LL(3rd)" and "adjusted HL(3rd), adjusted LH(3rd), and adjusted HH(3rd)" by performing a wavelet inverse transform. After that, as shown in FIG. 5, the third reconstructing unit 164*c* outputs "Level 3 output data", which is the data resulting from the reconstruction, to the second diffusion filter unit 162*b* at Level 2. The resolution of the "Level 3 output data" shown in FIG. 5 is "1/16" of the resolution of the B-mode data. It should be noted, however, that the "Level 3 output data" shown in FIG. 5 is, unlike in the conventional method, data obtained by synthesizing together the data of which the signal levels were adjusted after applying the non-linear anisotropic diffusion filter to the high-frequency decomposed image data at Level 3 and "filtered LL(3rd)". The resolution of the "Level 3 output data" shown in FIG. 5 is "1/16" of the resolution of the B-mode data.

At Level 2, as shown in FIG. 5, the second diffusion filter unit 162*b* calculates a structure tensor by using the "Level 3 output data" and detects edge information of the "Level 3 output data" from the structure tensor. After that, as shown in FIG. 5, the second diffusion filter unit 162*b* calculates a diffusion tensor from the structure tensor and the edge information and applies a non-linear anisotropic diffusion filter (2nd) to the "Level 3 output data" by using the calculated diffusion tensor. Subsequently, as shown in FIG. 5, the second diffusion filter unit 162*b* outputs the "filtered Level 3 output data" to the second reconstructing unit 164*b*.

Further, as shown in FIG. 5, the second diffusion filter unit 162*b* applies a non-linear anisotropic diffusion filter (2nd) to "HL(2nd), LH(2nd), and HH(2nd)" by using a diffusion filter coefficient of the diffusion tensor calculated from the "Level 3 output data" and outputs the result to the second adjusting unit 163*b*.

As shown in FIG. 5, the second adjusting unit 163*b* adjusts signal levels of "diffusion-filtered HL(2nd), diffusion-filtered LH(2nd), and diffusion-filtered HH(2nd)" on which the diffusion filtering process was performed, by using the edge information detected by the second diffusion filter unit 162*b*. After that, as shown in FIG. 5, the second adjusting unit 163*b* outputs "adjusted HL(2nd), adjusted LH(2nd), and adjusted HH(2nd)" to the second reconstructing unit 164*b*.

As shown in FIG. 5, the second reconstructing unit 164*b* synthesizes together the "filtered Level 3 output data" and "adjusted HL(2nd), adjusted LH(2nd), and adjusted HH(2nd)" by performing a wavelet inverse transform. After that, as shown in FIG. 5, the second reconstructing unit 164*b* outputs "Level 2 output data", which is the data resulting from the reconstruction, to the first diffusion filter unit 162*a* at Level 1. The resolution of the "Level 2 output data" shown in FIG. 5 is "1/4" of the resolution of the B-mode data. It should be noted, however, that the "Level 2 output data" shown in FIG. 5 is, unlike in the conventional method, data obtained by synthesizing together the data of which the signal levels were adjusted after applying the non-linear anisotropic diffusion filter to the high-frequency decomposed image data at Level 2 and the "filtered Level 3 output data". The resolution of the "Level 2 output data" shown in FIG. 5 is "1/4" of the resolution of the B-mode data.

At Level 1, as shown in FIG. 5, the first diffusion filter unit 162*a* calculates a structure tensor by using the "Level 2 output data" and detects edge information of the "Level 2 output data" from the structure tensor. After that, as shown in FIG. 5, the first diffusion filter unit 162*a* calculates a diffusion tensor from the structure tensor and the edge information and applies a non-linear anisotropic diffusion filter (1st) to the "Level 2 output data" by using the calculated diffusion tensor. Subsequently, as shown in FIG. 5, the first diffusion filter unit 162*a* outputs the "filtered Level 2 output data" to the first reconstructing unit 164*a*.

Further, as shown in FIG. 5, the first diffusion filter unit 162*a* applies a non-linear anisotropic diffusion filter (1st) to "HL(1st), LH(1st), and HH(1st)" by using a diffusion filter coefficient of the diffusion tensor calculated from the "Level 2 output data" and outputs the result to the first adjusting unit 163*a*.

As shown in FIG. 5, the first adjusting unit 163a adjusts signal levels of "diffusion-filtered HL(1st), diffusion-filtered LH(1st), and diffusion-filtered HH(1st)" on which the diffusion filtering process was performed, by using the edge information detected by the first diffusion filter unit 162a. After that, as shown in FIG. 5, the first adjusting unit 163a outputs "adjusted HL(1st), adjusted LH(1st), and adjusted HH(1st)" to the first reconstructing unit 164a.

As shown in FIG. 5, the first reconstructing unit 164a synthesizes together the "filtered Level 2 output data" and "adjusted HL(1st), adjusted LH(1st), and adjusted HH(1st)" by performing a wavelet inverse transform. After that, as shown in FIG. 5, the first reconstructing unit 164a outputs "Level 1 output data", which is the data resulting from the reconstruction, to the image generating unit 15 as "corrected B-mode data". The image generating unit 15 generates display-purpose ultrasound image data by performing a scan convert process on the corrected B-mode data. The resolution of the "Level 1 output data" shown in FIG. 5 is equal to the resolution of the B-mode data. It should be noted, however, that the "Level 1 output data" shown in FIG. 5 is, unlike in the conventional method, data obtained by synthesizing together the data of which the signal levels were adjusted after applying the non-linear anisotropic diffusion filter to the high-frequency decomposed image data at Level 1 and the "filtered Level 2 output data". The resolution of the "Level 1 output data" shown in FIG. 5 is equal to the resolution of the B-mode data.

Next, the processes performed by the diffusion filter unit 162 and the adjusting unit 163 according to the present embodiment described above will be further explained by using mathematical expressions and the like.

The diffusion filter unit 162 calculates the structure tensor by differentiating a pixel level (a brightness value) of the input image data in the horizontal direction (the widthwise direction or the x direction) and the vertical direction (the lengthwise direction or the y direction). The structure tensor is a tensor calculated for the purpose of detecting the magnitude and the direction of the edge. An eigenvalue of the structure tensor is associated with the magnitude of the edge, whereas an eigenvector of the structure tensor expresses the direction of the edge. A structure tensor "S" can be defined as shown in Expression (1) below:

$$S = Gp * \begin{pmatrix} I_x^2 & I_x I_y \\ I_x I_y & I_y^2 \end{pmatrix} = \begin{pmatrix} Gp * I_x^2 & Gp * (I_x I_y) \\ Gp * (I_x I_y) & Gp * I_y^2 \end{pmatrix} = \begin{pmatrix} s_{11} & s_{12} \\ s_{12} & s_{22} \end{pmatrix} \quad (1)$$

In this situation, "$I_x$" in Expression (1) denotes an x-direction spatial derivative of a pixel level "I" of the input image data, whereas "$I_y$" in Expression (1) denotes a y-direction spatial derivative of "I". Further, "$G\rho$" denotes a two-dimensional Gaussian function, whereas the operator "*" denotes a convolution. For example, the third diffusion filter unit 162c calculates the structure tensor "$s_{11}, s_{12}, s_{22}$" shown in Expression (1), by differentiating "LL(3rd)" in the horizontal direction (the widthwise direction or the x direction) and the vertical direction (the lengthwise direction or the y direction).

To calculate the structure tensor, it is not necessary to precisely follow the method shown above. Alternatively, it is also acceptable to apply a sobel filter at the first stage of the process, instead of calculating "$I_x$" and "$I_y$".

After that, the diffusion filter unit 162 detects the edge information (the position, the magnitude, and the direction of the edge) from each of the elements of the calculated structure tensor. More specifically, the diffusion filter unit 162 detects the edge information from each of the elements of the structure tensor and further calculates the diffusion filter coefficient used in the calculation of the diffusion tensor. After that, the diffusion filter unit 162 calculates the diffusion tensor. A diffusion tensor (D) can be defined as shown in Expression (2) below:

$$D = \begin{pmatrix} d_{11} & d_{12} \\ d_{12} & d_{22} \end{pmatrix} = R \begin{pmatrix} \lambda_1 & 0 \\ 0 & \lambda_2 \end{pmatrix} R^T \quad (2)$$

In this situation, "R" in Expression (2) denotes a rotation matrix, whereas "$R^T$" denotes a transposed matrix of "R". Further, "$\lambda_1, \lambda_2$" in Expression (2) are diffusion filter coefficients calculated from the edge information. For example, the third diffusion filter unit 162c calculates a diffusion tensor "$d_{11}, d_{12}, d_{22}$" of "LL(3rd)" by using Expression (2).

Further, the diffusion filter unit 162 applies a non-linear anisotropic diffusion filter based on the diffusion tensor to "I". The non-linear anisotropic diffusion filter can be expressed as shown in Expression (3) below, which is a partial differential equation.

$$\frac{\partial I}{\partial t} = div[D \nabla I] \quad (3)$$

In this situation, "$\nabla I$ (nabla I)" in Expression (3) is a gradient vector of "I", whereas "t" in Expression (3) is a time that is related to the process. Further, "div" in Expression (3) is a divergence.

In other words, the calculating process "$D \nabla I$" performed by the diffusion filter unit 162 in Expression (3) is a calculating process to multiply a specific direction with respect to the gradient vector of each of the pixels and the direction perpendicular to the specific direction by "$\lambda_1$" and "$\lambda_2$", respectively. In this situation, the "specific direction" is the direction of the edge of the image data, whereas the diffusion filter coefficients are calculated according to the magnitude of the edge.

Further, the diffusion filter unit 162 performs the non-linear anisotropic diffusion filtering process by performing the numeric value analytical calculation using the partial differential equation shown in Expression (3) either once or multiple times repeatedly. For example, at the time "t", based on the pixel levels of a pixel at a point and a plurality of points (e.g., 9 points) in the surrounding of the pixel and the values of the elements of the diffusion tensor, the diffusion filter unit 162 calculates new pixel levels of the points at a time "t+Δt". After that, by using "t+Δt" as a new "t", the diffusion unit 162 repeats the same calculation once or multiple times. For example, the third diffusion filter unit 162c performs this non-linear anisotropic diffusion filtering process on "LL(3rd)" and "HL(3rd), LH(3rd), and HH(3rd)".

For the purpose of being able to change the method for calculating "$\lambda_1, \lambda_2$" depending on the characteristic of each of the ultrasound images in different diagnostic fields, it is desirable to prepare general expressions, so that it is possible to make adjustments with one or more parameters.

Further, the adjusting unit 163 adjusts the signal levels of the diffusion-filtered high-frequency decomposed image data, i.e., "diffusion-filtered HL, diffusion-filtered LH, and diffusion-filtered HH", based on the "eigenvalue of the structure tensor serving as the edge information". As described above, the eigenvalue of the structure tensor indicates the magnitude of the edge. Thus, the adjusting unit 163 calculates, for each of the pixels, the product of the magnitude of the edge normalized based on the eigenvalue of the structure tensor and each of the pieces of high-frequency decomposed image data. Further, by multiplying the calculation result by a control coefficient set for each of the pieces of high-frequency decomposed image data, the adjusting unit 163 performs a high-frequency level adjusting process. Alternatively, the adjusting unit 163 may perform a high-frequency level adjusting process by setting a threshold value for the magnitude of the edge and, while considering components exceeding the threshold value as the edge, multiplying the data in the area other than the edge by the control coefficient corresponding to each of the pieces of high-frequency decomposed image data.

Figure 6A:
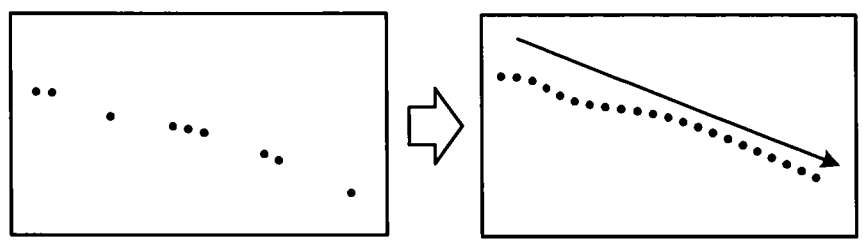
FIG. 6A and FIG. 6B are drawings for explaining the advantageous effects of the present embodiment.
Figure 6B:

As explained above, according to the present embodiment, the non-linear anisotropic diffusion filter is applied even to the high-frequency decomposed image data. More specifically, according to the present embodiment, the non-linear anisotropic diffusion filter is applied to the high-frequency decomposed image data by using the structure tensor and the edge information of either the low-frequency decomposed image data or the reconstructed data from the level immediately underneath. FIGS. 6A and 6B are drawings for explaining advantageous effects of the present embodiment.

As a result of applying the non-linear anisotropic diffusion filter to the high-frequency decomposed image data, it is possible to adjust the structure extending in a diagonal direction, which seems unclear in the high-frequency decomposed image, so as to seem continuous in a diagonal direction as shown in FIG. 6A. More specifically, by adjusting the diffusion filter coefficients, it is possible to apply an appropriate edge enhancement even to the high-frequency decomposed image data. In the present embodiment, the reconstructing process is performed after performing the signal level adjusting process on the high-frequency decomposed image data to which the diffusion filtering process was applied in this manner. As a result, in the ultrasound image that is generated and displayed after the scan convert process is performed on the corrected B-mode data output by the first reconstructing unit 164*a* according to the first embodiment, the diagonal structure has a substantially smooth shape, as shown in FIG. 6B.

Figure 9:
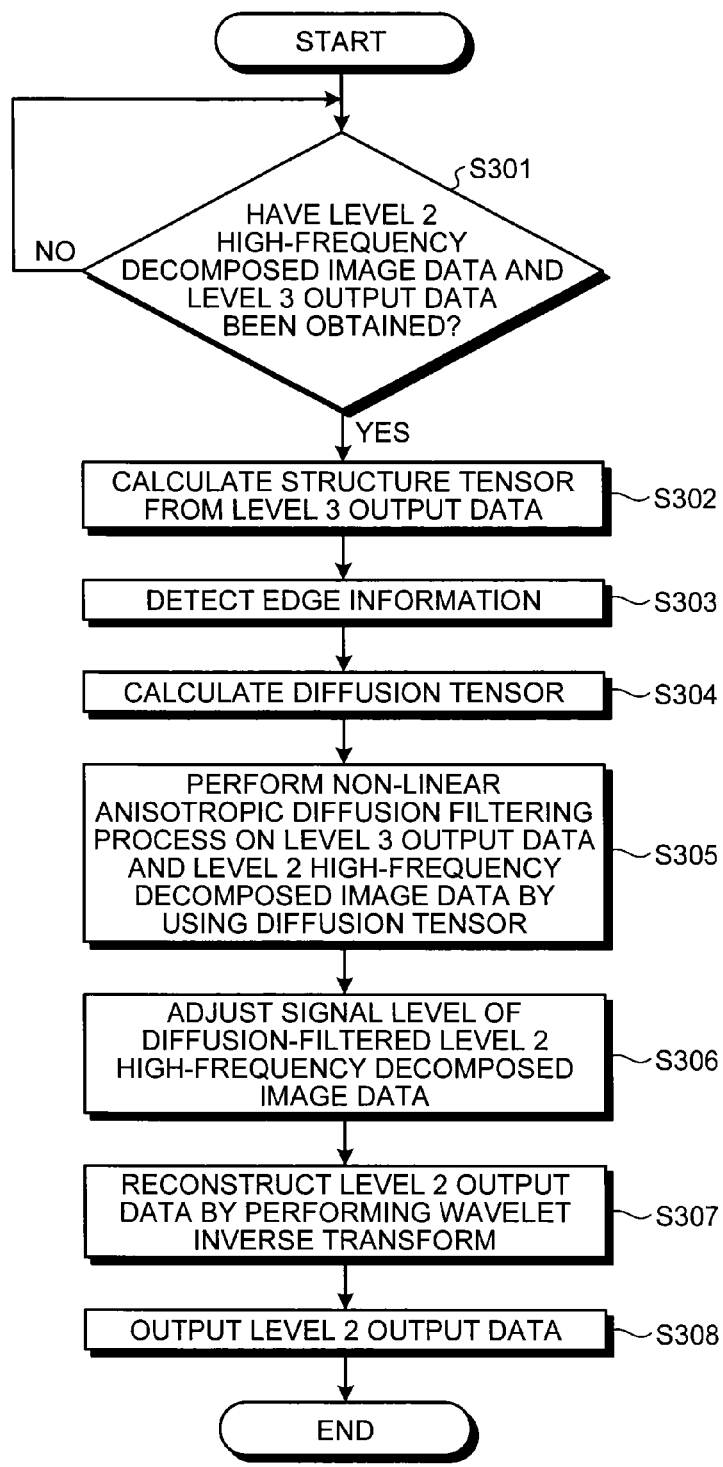
FIG. 9 is a flowchart for explaining a process performed at Level 2 by the image processing unit according to the present embodiment.
Figure 10:
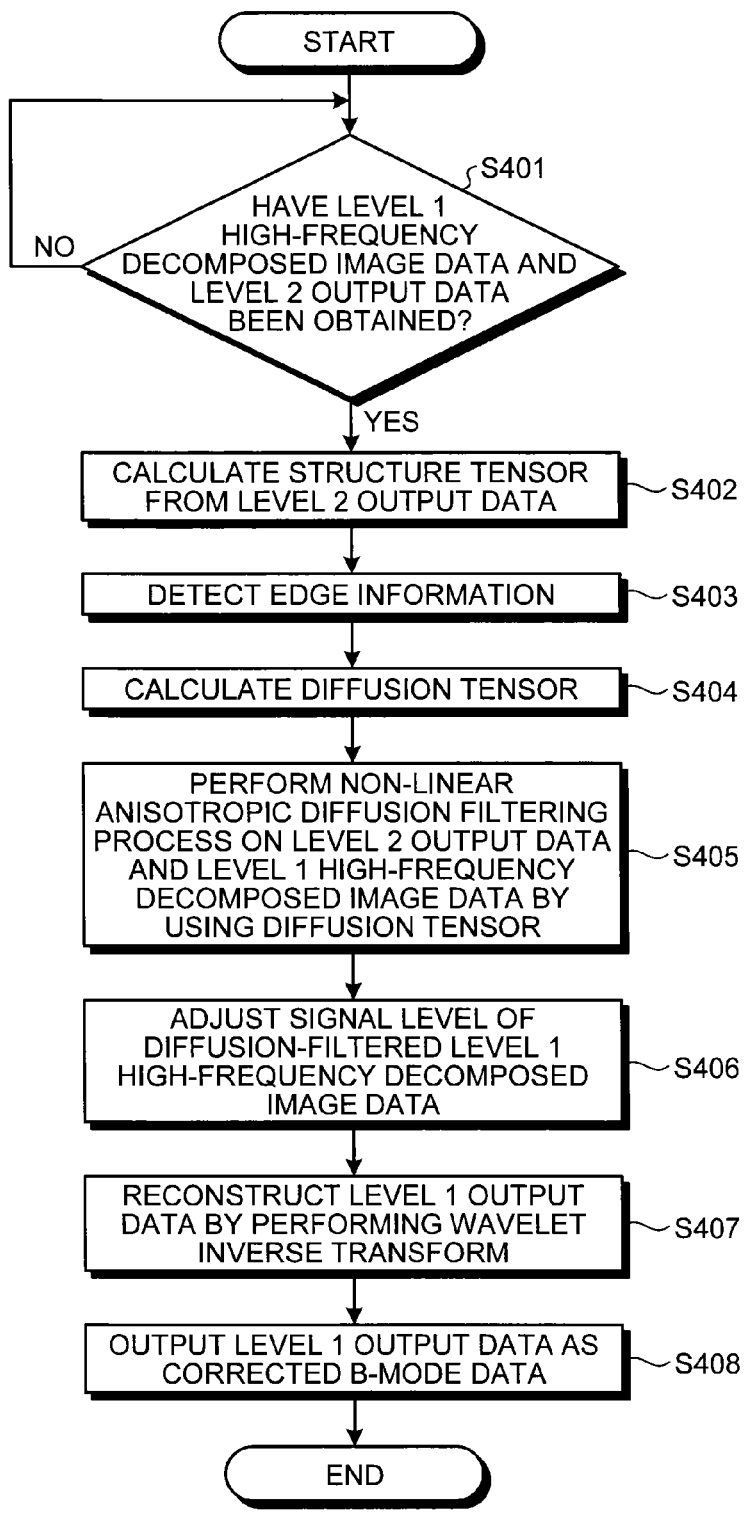
FIG. 10 is a flowchart for explaining a process performed at Level 1 by the image processing unit according to the present embodiment.

Next, processes performed by the ultrasound diagnosis apparatus according to the present embodiment will be explained, with reference to FIGS. 7 to 10. FIG. 7 is a flowchart for explaining a process performed by the decomposing unit according to the present embodiment. FIG. 8 is a flowchart for explaining a process performed at Level 3 by the image processing unit according to the present embodiment. FIG. 9 is a flowchart for explaining a process performed at Level 2 by the image processing unit according to the present embodiment. FIG. 10 is a flowchart for explaining a process performed at Level 1 by the image processing unit according to the present embodiment.

As shown in FIG. 7, the first decomposing unit 161*a* included in the ultrasound diagnosis apparatus according to the present embodiment judges whether B-mode data has been stored into the image memory 17 (step S101). In this situation, if no B-mode data has been stored (step S101: No), the first decomposing unit 161*a* goes into a standby state.

On the contrary, if B-mode data has been stored (step S101: Yes), the first decomposing unit 161*a* decomposes the B-mode data into low-frequency decomposed image data and high-frequency decomposed image data at Level 1, by performing a wavelet transform (step S102).

After that, the second decomposing unit 161*b* decomposes the low-frequency decomposed image data at Level 1 into low-frequency decomposed image data and high-frequency decomposed image data at Level 2, by performing a wavelet transform (step S103).

Subsequently, the third decomposing unit 161*c* decomposes the low-frequency decomposed image data at Level 2 into low-frequency decomposed image data and high-frequency decomposed image data at Level 3, by performing a wavelet transform (step S104), and the decomposing process is thus ended.

After that, the process at Level 3 is performed as shown in FIG. 8. More specifically, as shown in FIG. 8, the third diffusion filter unit 162*c* judges whether the low-frequency decomposed image data and the high-frequency decomposed image data at Level 3 have been obtained (step S201). In this situation, if the judgment result is in the negative (step S201: No), the third diffusion filter unit 162*c* goes into a standby state.

On the contrary, if the low-frequency decomposed image data and the high-frequency decomposed image data at Level 3 have been obtained (step S201: Yes), the third diffusion filter unit 162*c* calculates a structure tensor from the Level 3 low-frequency decomposed image data (step S202), and further detects edge information from the structure tensor (step S203). Subsequently, the third diffusion filter unit 162*c* calculates a diffusion tensor from the structure tensor and the edge information (step S204).

After that, the third diffusion filter unit 162*c* performs a non-linear anisotropic diffusion filtering process on the Level 3 low-frequency decomposed image data and the Level 3 high-frequency decomposed image data by using the diffusion tensor (step S205).

Further, the third adjusting unit 163*c* adjusts the signal level of the Level 3 high-frequency decomposed image data on which the diffusion filtering process was performed (step S206). The third reconstructing unit 164*c* reconstructs (synthesizes the data to obtain) Level 3 output data by performing a wavelet inverse transform (step S207). After that, the third reconstructing unit 164*c* outputs the Level 3 output data to the second diffusion filter unit 162*b* (step S208), and the process at Level 3 is thus ended.

After that, the process at Level 2 is performed as shown in FIG. 9. More specifically, as shown in FIG. 9, the second diffusion filter unit 162*b* judges whether the Level 2 high-frequency decomposed image data and the Level 3 output data have been obtained (step S301). In this situation, if the judgment result is in the negative (step S301: No), the second diffusion filter unit 162*b* goes into a standby state.

On the contrary, if the Level 2 high-frequency decomposed image data and the Level 3 output data have been obtained (step S301: Yes), the second diffusion filter unit 162*b* calculates a structure tensor from the Level 3 output data (step S302), and further detects edge information from the structure tensor (step S303). Subsequently, the second diffusion filter unit 162*b* calculates a diffusion tensor from the structure tensor and the edge information (step S304).

After that, the second diffusion filter unit 162*b* performs a non-linear anisotropic diffusion filtering process on the Level 3 output data and the Level 2 high-frequency decomposed image data by using the diffusion tensor (step S305).

Further, the second adjusting unit 163*b* adjusts the signal level of the Level 2 high-frequency decomposed image data on which the diffusion filtering process was performed (step S306). The second reconstructing unit 164b reconstructs (synthesizes the data to obtain) Level 2 output data by performing a wavelet inverse transform (step S307). After that, the second reconstructing unit 164b outputs the Level 2 output data to the first diffusion filter unit 162a (step S308), and the process at Level 2 is thus ended.

After that, the process at Level 1 is performed as shown in FIG. 10. More specifically, as shown in FIG. 10, the first diffusion filter unit 162a judges whether the Level 1 high-frequency decomposed image data and the Level 2 output data have been obtained (step S401). In this situation, if the judgment result is in the negative (step S401: No), the first diffusion filter unit 162a goes into a standby state.

On the contrary, if the Level 1 high-frequency decomposed image data and the Level 2 output data have been obtained (step S401: Yes), the first diffusion filter unit 162a calculates a structure tensor from the Level 2 output data (step S402), and further detects edge information from the structure tensor (step S403). Subsequently, the first diffusion filter unit 162a calculates a diffusion tensor from the structure tensor and the edge information (step S404).

After that, the first diffusion filter unit 162a performs a non-linear anisotropic diffusion filtering process on the Level 2 output data and the Level 1 high-frequency decomposed image data by using the diffusion tensor (step S405).

Further, the first adjusting unit 163a adjusts the signal level of the Level 1 high-frequency decomposed image data on which the diffusion filtering process was performed (step S406). The first reconstructing unit 164a reconstructs (synthesizes the data to obtain) Level 1 output data by performing a wavelet inverse transform (step S407). After that, the first reconstructing unit 164a outputs the Level 1 output data to the image generating unit 15 as corrected B-mode data (step S408), and the process at Level 1 is thus ended.

As explained above, according to the present embodiment, similarly to the conventional method, the edge portion is enhanced by using the non-linear anisotropic diffusion filters, the speckles are eliminated by performing the diffusion processes on the portion other than the edge portion, and further, the processing load required by the non-linear anisotropic filtering processes is reduced by using the multi-resolution analysis in combination.

However, according to the present embodiment, unlike the conventional method, the non-linear anisotropic diffusion filters are applied even to the high-frequency decomposed image data. As a result, according to the present embodiment, it is possible to increase the degree of freedom in setting the diffusion filter coefficients. It is therefore possible to adjust the diffusion filter coefficients so as to decrease the occurrence of the stair-stepped structure in the ultrasound image. As a result, according to the present embodiment, it is possible to generate an ultrasound image in which the edge is enhanced without causing the feeling that something is wrong with the ultrasound image and from which the speckles are eliminated.

Further, according to the present embodiment, the non-linear anisotropic diffusion filter is applied to the high-frequency decomposed image data, by using the edge information of either the low-frequency decomposed image data or the reconstructed data from the level immediately underneath, instead of the edge information of the high-frequency decomposed image data. In other words, according to the present embodiment, the diffusion tensor of the high-frequency decomposed image data is not calculated, and the diffusion tensor is calculated only once at each of the hierarchical levels (at each of the levels). Thus, the additional calculation amount caused by the process of applying the diffusion filter to the high-frequency component is reduced. As a result, according to the present embodiment, it is possible to perform the calculation at a high speed in the speckle eliminating process.

The exemplary embodiments described above are applicable also to the situation where the number of levels is an arbitrary natural number that is two or larger. Also, the exemplary embodiments described above are applicable to the situation where the multi-resolution analysis is performed by using a method (e.g., a Laplacian pyramid method) other than the "wavelet transform and wavelet inverse transform" method. Further, the exemplary embodiments described above are applicable to the situation where "B-mode image data" is used as the ultrasound image data. Furthermore, the exemplary embodiments described above are also applicable to the situation where the ultrasound image data is three-dimensional ultrasound image data generated by using a 2D probe or a mechanical scan probe.

The exemplary embodiments above are explained by using the example where the processes are performed by the ultrasound diagnosis apparatus. However, the image processing processes explained in the exemplary embodiments above may be performed by an image processing apparatus that is provided independently of the ultrasound diagnosis apparatus. More specifically, an arrangement is acceptable in which an image processing apparatus having the functions of the image processing unit 16 shown in FIG. 1 receives the ultrasound image data from the ultrasound diagnosis apparatus or from a database of a Picture Archiving and Communication System (PACS) or a database of an electronic medical record system and performs the image processing processes described above thereon. Further, such an image processing apparatus may perform the image processing processes explained in the exemplary embodiments above on medical image data other than ultrasound image data. Examples of such medical image data include: X-ray Computed Tomography (CT) image data generated by an X-ray CT apparatus; Magnetic Resonance Imaging (MRI) image data generated by an MRI apparatus; and X-ray image data generated by an X-ray diagnosis apparatus.

The constituent elements of the apparatuses shown in the drawings are based on functional concepts. Thus, it is not necessary to physically configure the elements as indicated in the drawings. In other words, the specific mode of distribution and integration of the apparatuses is not limited to those shown in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a Central Processing Unit (CPU) and a computer program that is analyzed and executed by the CPU or may be realized as hardware using wired logic.

It is possible to realize the image processing method explained in the exemplary embodiments by causing a computer such as a personal computer or a workstation to execute an image processing computer program prepared in advance. It is possible to distribute such an image processing computer program via a network such as the Internet. Further, the image processing computer program may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like, and may be executed as being read by a computer from the recoding medium.

As explained above, according to the present embodiment, it is possible to generate an ultrasound image in which the edge is enhanced without causing the feeling that something is wrong with the ultrasound image and from which the speckles are eliminated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
   decomposing circuitry configured to decompose ultrasound image data into low-frequency decomposed image data and high-frequency decomposed image data at each of a predetermined number of hierarchical levels, by performing a hierarchical multi-resolution analysis;
   diffusion filter circuitry configured to apply, at a lowest hierarchical level of the predetermined number of hierarchical levels, a non-linear anisotropic diffusion filter to the low-frequency decomposed image data and the high-frequency decomposed image data at the lowest hierarchical level, configured to apply, at each of the hierarchical levels higher than the lowest hierarchical level, a non-linear anisotropic diffusion filter to data output from a hierarchical level immediately underneath that has been reconstructed by performing a multi-resolution analysis and to the high-frequency decomposed image data at that hierarchical level, and configured to generate, for each of the hierarchical levels, edge information of a signal either from the low-frequency decomposed image data at the lowest hierarchical level or from the data output from the hierarchical level immediately underneath;
   adjusting circuitry configured to adjust a signal level of the high-frequency decomposed image data to which the non-linear anisotropic diffusion filter was applied, based on the edge information generated by the diffusion filter circuitry on the same hierarchical level as the hierarchical level of the high-frequency decomposed image data at each of the hierarchical levels; and
   reconstructing circuitry configured to:
      reconstruct data by performing the multi-resolution analysis, from the data that has been processed by the diffusion filter circuitry and was not used in the process performed by the adjusting circuitry and the data that has been processed by the adjusting circuitry at the same hierarchical level,
      output the reconstructed data as the output data to be processed by the diffusion filter circuitry at the hierarchical level immediately above, and
      obtain the reconstructed data as corrected data of the ultrasound image data at the highest hierarchical level,
   wherein at the lowest hierarchical level, the diffusion filter circuitry applies the non-linear anisotropic diffusion filter to the high-frequency decomposed image data at the lowest hierarchical level by using a diffusion filter coefficient calculated based on a structure tensor and the edge information detected from the low-frequency decomposed image data at the lowest hierarchical level, whereas at each of the hierarchical levels higher than the lowest hierarchical level, the diffusion filter circuitry applies the non-linear anisotropic diffusion filter to the high-frequency decomposed image data at that hierarchical level by using a diffusion filter coefficient calculated based on a structure tensor and the edge information detected from the output data that is output by the reconstructing circuitry at the hierarchical level immediately underneath.

2. An image processing apparatus comprising:
   decomposing circuitry configured to decompose medical image data into low-frequency decomposed image data and high-frequency decomposed image data at each of a predetermined number of hierarchical levels, by performing a hierarchical multi-resolution analysis;
   diffusion filter circuitry configured to apply, at a lowest hierarchical level of the predetermined number of hierarchical levels, a non-linear anisotropic diffusion filter to the low-frequency decomposed image data and the high-frequency decomposed image data at the lowest hierarchical level, configured to apply, at each of the hierarchical levels higher than the lowest hierarchical level, a non-linear anisotropic diffusion filter to data output from a hierarchical level immediately underneath that has been reconstructed by performing a multi-resolution analysis and to the high-frequency decomposed image data at that hierarchical level, and configured to generate, for each of the hierarchical levels, edge information of a signal either from the low-frequency decomposed image data at the lowest hierarchical level or from the data output from the hierarchical level immediately underneath;
   adjusting circuitry configured to adjust a signal level of the high-frequency decomposed image data to which the non-linear anisotropic diffusion filter was applied, based on the edge information generated by the diffusion filter circuitry on the same hierarchical level as the hierarchical level of the high-frequency decomposed image data at each of the hierarchical levels; and
   reconstructing circuitry configured to:
      reconstruct data by performing the multi-resolution analysis, from the data that has been processed by the diffusion filter circuitry and was not used in the process performed by the adjusting circuitry and the data that has been processed by the adjusting circuitry at the same hierarchical level,
      output the reconstructed data as the output data to be processed by the diffusion filter circuitry at the hierarchical level immediately above, and
      obtain the reconstructed data as corrected data of the ultrasound image data at the highest hierarchical level,
   wherein at the lowest hierarchical level, the diffusion filter circuitry applies the non-linear anisotropic diffusion filter to the high-frequency decomposed image data at the lowest hierarchical level by using a diffusion filter coefficient calculated based on a structure tensor and the edge information detected from the low-frequency decomposed image data at the lowest hierarchical level, whereas at each of the hierarchical levels higher than the lowest hierarchical level, the diffusion filter circuitry applies the non-linear anisotropic diffusion filter to the high-frequency decomposed image data at that hierarchical level by using a diffusion filter coefficient calculated based on a structure tensor and the edge information detected from the output data that is output by the reconstructing circuitry at the hierarchical level immediately underneath.

3. An image processing method comprising:
a process performed by decomposing circuitry to decompose medical image data into low-frequency decomposed image data and high-frequency decomposed image data at each of a predetermined number of hierarchical levels, by performing a hierarchical multi-resolution analysis;
a process performed by diffusion filter circuitry to apply, at a lowest hierarchical level of the predetermined number of hierarchical levels, a non-linear anisotropic diffusion filter to the low-frequency decomposed image data and the high-frequency decomposed image data at the lowest hierarchical level, to apply, at each of the hierarchical levels higher than the lowest hierarchical level, a non-linear anisotropic diffusion filter to data output from a hierarchical level immediately underneath that has been reconstructed by performing a multi-resolution analysis and to the high-frequency decomposed image data at that hierarchical level, and to generate, for each of the hierarchical levels, edge information of a signal either from the low-frequency decomposed image data at the lowest hierarchical level or from the data output from the hierarchical level immediately underneath;
a process performed by adjusting circuitry to adjust a signal level of the high-frequency decomposed image data to which the non-linear anisotropic diffusion filter was applied, based on the edge information generated by the diffusion filter circuitry on the same hierarchical level as the hierarchical level of the high-frequency decomposed image data at each of the hierarchical levels; and
a process performed by reconstructing circuitry to:
reconstruct data by performing the multi-resolution analysis, from the data that has been processed by the diffusion filter circuitry and was not used in the process performed by the adjusting circuitry and the data that has been processed by the adjusting circuitry at the same hierarchical level,
output the reconstructed data as the output data to be processed by the diffusion filter circuitry at the hierarchical level immediately above, and
obtain the reconstructed data as corrected data of the ultrasound image data at the highest hierarchical level,
at the lowest hierarchical level, the process performed by the diffusion filter circuitry includes applying the non-linear anisotropic diffusion filter to the high-frequency decomposed image data at the lowest hierarchical level by using a diffusion filter coefficient calculated based on a structure tensor and the edge information detected from the low-frequency decomposed image data at the lowest hierarchical level, whereas at each of the hierarchical levels higher than the lowest hierarchical level, the process performed by the diffusion filter circuitry includes applying the non-linear anisotropic diffusion filter to the high-frequency decomposed image data at that hierarchical level by using a diffusion filter coefficient calculated based on a structure tensor and the edge information detected from the output data that is output by the reconstructing circuitry at the hierarchical level immediately underneath.

4. The ultrasound diagnosis apparatus according to claim 1, wherein
data output from the highest hierarchical level has a resolution equal to a resolution of the ultrasound image data,
data output from a level underneath the highest hierarchical level has a resolution equal to ¼ the resolution of the ultrasound image data, and
data output from a level underneath the level underneath the highest hierarchical level has a resolution equal to ¹⁄₁₆ the resolution of the ultrasound image data.

* * * * *